United States Patent [19]
Sanghvi et al.

[11] Patent Number: 5,965,167
[45] Date of Patent: Oct. 12, 1999

[54] DOSAGE UNITS

[76] Inventors: Pradeepkumar P. Sanghvi, 2515 Isham Randol Ph Dr., Herndon, Va. 20171; David P. Prior, 19925 Upland Terreace, Ashburn, Va. 20147; Djelila Mezaache, 8609 Accoueek St., Laurel, Md. 20724; Scott J. Szedlock, 4447 Fair Stone Dr.,No. 102, Fairfax, Va. 22033

[21] Appl. No.: 08/946,069

[22] Filed: Oct. 7, 1997

[51] Int. Cl.⁶ .............................. A61K 9/16; A61K 9/50
[52] U.S. Cl. .................. 424/490; 424/489; 424/461; 424/464; 424/494
[58] Field of Search .............................. 264/15; 424/489, 424/490, 464

[56] References Cited

U.S. PATENT DOCUMENTS

| | | | |
|---|---|---|---|
| 5,023,245 | 6/1991 | Kuhrts | 514/54 |
| 5,037,658 | 8/1991 | Urban et al. | 424/469 |
| 5,047,427 | 9/1991 | Williamson | 514/557 |
| 5,118,510 | 6/1992 | Kuhrts | 424/451 |
| 5,126,145 | 6/1992 | Evenstad et al. | 424/465 |
| 5,292,534 | 3/1994 | Valentine et al. | 424/451 |
| 5,427,799 | 6/1995 | Valentine et al. | 424/451 |
| 5,683,720 | 11/1997 | Myers et al. | 424/489 |
| 5,849,223 | 12/1998 | Myers et al. | 264/15 |

*Primary Examiner*—Thurman K. Page
*Assistant Examiner*—William E. Benston, Jr.

[57] ABSTRACT

The invention relates to a novel dosage unit for the sustained-release delivery of active agents as well as compositions and methods for making same.

14 Claims, 2 Drawing Sheets

DOSAGE UNITS

BACKGROUND OF THE INVENTION

Certain bio-affecting agents, or active agents, are most effective when delivered to a host via dosage units which mask their taste and/or which release them over extended periods of time, that is, in about 6 to about 24 hours. Products in which the unpleasant flavor of the drug is undetected are termed "taste-masked." Products which deliver agents over extended time periods are generally termed "sustained release" or "extended release." Among the active agents which are best administered over extended periods are those whose loading doses give adverse reactions and those required to be administered multiple times in a day.

Oral taste-masked and sustained release dosage forms are conventionally prepared by coating drug-containing spheres with materials which alter, respectively, the taste and the rate at which the drug(s) in the spheres become available to the consumer. The application of suitable coatings is complicated when the spheres are too friable, or fragile, to withstand the coating process.

Certain drugs are known to produce very friable spheres. Among them are niacin, acetaminophen (APAP), and aspirin.

The unpalatable nature of APAP and aspirin make them candidates for taste-masked products. Also, when used to treat chronic or long-term pain, they are used several times a day. Patient compliance is improved by masking the taste of these agents.

Niacin, a cholesterol-lowering agent, is a candidate for use in a sustained release dosage unit. When ingested orally, it produces, in significant numbers of consumers, a "flushing," or burning, sensation and gastrointestinal discomfort. These side effects lower patient compliance.

APAP and aspirin are well-known analgesics. When used to treat chronic, or long-term, discomfort, they are administered several times a day. Thus, sustained release forms of these agents are desirable.

Thus, taste-masked/sustained release dosage units of niacin, APAP, aspirin or similar drugs are desirable to achieve therapeutic effects and encourage patient compliance.

Niacin products have been made in the past using technologies such as the following:

U.S. Pat. No. 5,023,245 teaches niacin formulations containing niacin (nicotinic acid), gel-forming dietary fiber and magnesium carbonate. The formulations are taken in capsule form five times a day, with 100 mg of niacin ingested with each dose.

U.S. Pat. No. 5,047,427 shows the treatment of diabetes with a pyruvate salt or with niacin. The agents are administered several times a day. One to three grams of niacin is used daily.

U.S. Pat. No. 5,118,510 describes a drink mix containing coated granules of: niacin, guar gum, a gas-forming agent, and ethyl cellulose. As gas (i.e., carbon dioxide) forms in the stomach, the niacin is released.

U.S. Pat. No. 5,126,145 deals with a controlled release niacin tablet containing a high-viscosity hydroxypropylmethylcellulose (HPMC), a low-viscosity HPMC, hydrogenated vegetable oil or stearic acid, and niacin. From 10% to 35% of the niacin dissolves within two hours of ingestion.

U.S. Pat. Nos. 5,292,534 and 5,427,799 relate to niacin capsules or tablets containing the agent along with xanthan gum and a lubricant. The presence of xanthan gum is taught as diminishing the "flushing" normally associated with niacin use.

SUMMARY OF THE INVENTION

Applicants have discovered that a novel combination of active agents and processing aids can be made into highly stable microspheres using liquiflash technology. The microspheres are then coated with certain polymeric blends to produce coated spheres which yield sustained-release dosage units. Niacin, APAP and aspirin are among the active agents which are effectively administered using these dosage units.

The dosage units of the invention are characterized by the stability of the bio-affecting microspheres therein and the sustained-release dissolution profile of the units. Oral dosage forms, such as capsules, sachets and tablets, are typical.

Because they are spherical, the microspheres of the invention are readily flowable, so that processing and delivery to the consumer are facilitated, regardless of the type of product in which they are used.

DETAILED DESCRIPTION OF THE INVENTION

Figure 1:
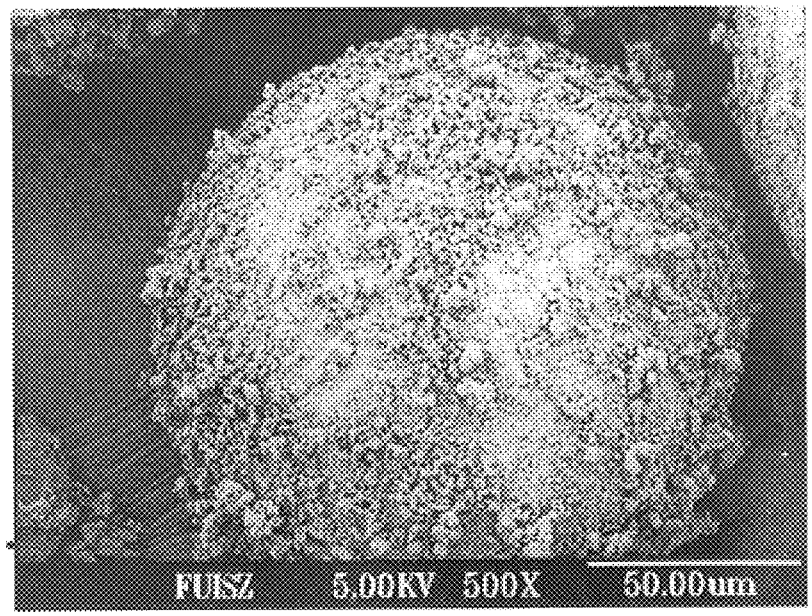
FIG. 1 is an electromicrograph, at 500x magnification, of a 100% niacin microsphere.

The invention deals with novel dosage units and with compositions and methods used to make them.

Unless otherwise stated herein, all parts and percentages recited are weight parts and percentages based on total composition weight.

The dosage units are stable, sustained release products for delivering active agents, such as niacin, APAP, and aspirin.

By "sustained release", applicants refer to a delayed release pattern, such as may be achieved using pharmaceutical excipients and suitable coating(s). Using such features, $T_{max}$ (or time to maximum active agent release into the bloodstream) occurs later than it would occur when delivering the same active agent using an immediate release pattern.

When an agent such as niacin is delivered via a sustained release dosage form, the side effects profile associated with its use is expected to be less severe, resulting in improved patient compliance.

The Compositions

The compositions from which the dosage units of the invention are made involve two components: a microsphere substrate and a coating.

The microsphere substrate is made by subjecting a suitable binary feedstock to spheronization conditions to produce solid microspheres having particle sizes of 500 microns or less. By "binary", applicants mean feedstocks containing only one active agent component and one processing aid component. The feedstock used to make the microspheres of this invention includes at least one active agent and at least one processing aid. Two-component microspheres are preferred.

Monodispersed microspheres such as those made using liquiflash conditions are useful. Suitable processes and devices are described below.

The active agents useful herein include a variety of bio-affecting substances. Among these agents are: niacin, acetaminophen (APAP), and aspirin. Mixtures of these and other bio-affecting agents can be used.

Quantities of active agents in the final dosage forms range from about 10 mg to 1,500 mg and beyond. When niacin is the active agent, amounts of about 100 to about 1,000 are typical.

"Niacin" refers to nicotinic acid and all pharmaceutically acceptable equivalents thereto. Of these, Niacin, either alone or in combination with one or more derivatives can function ad the niacin component. Niacin per se is preferred.

The processing aid used herein is one of a group of materials, many of which are commonly called "waxes." Among these are: carnauba wax, White wax, and mixtures. Carnauba wax is generally used.

Materials which are not "waxes" can also be used. Polymers such as polyvinylpyrrolidone (PVP) as well as simple molecules, e.g., Compritol 888ATO, cetyl alcohol, and stearic acid are operable.

Other ingredients conventionally used in oral dosage formulations can be included in suitable amounts. Thus, from about 0% to about 80% of one or more lubricants, colorants, flavorants, fillers, binders, flow agents and the like can be used. These ingredients are typically combined with preformed microspheres.

The microspheres used herein generally contain only the active agent(s) and the processing aid(s).

Figure 2:
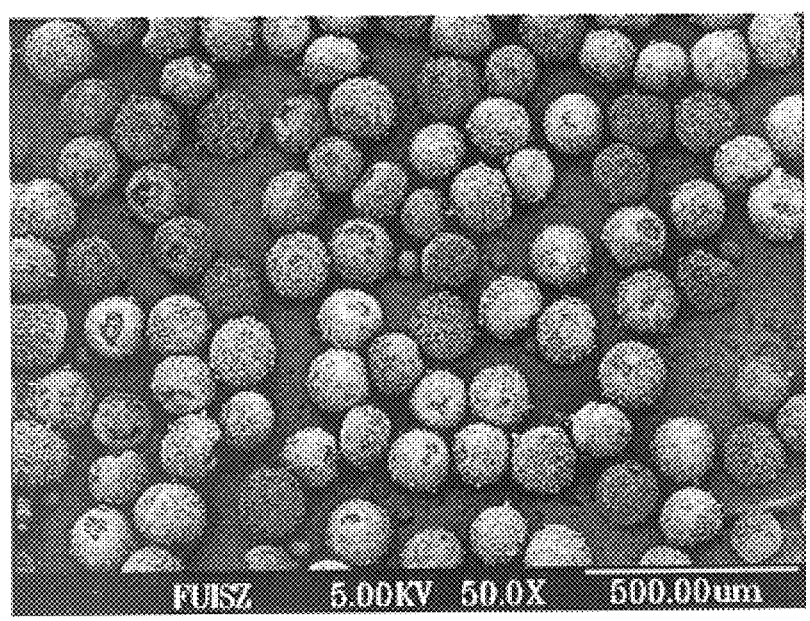
FIG. 2 is a 50x magnification electromicrograph of 100% niacin microspheres.
Figure 3:
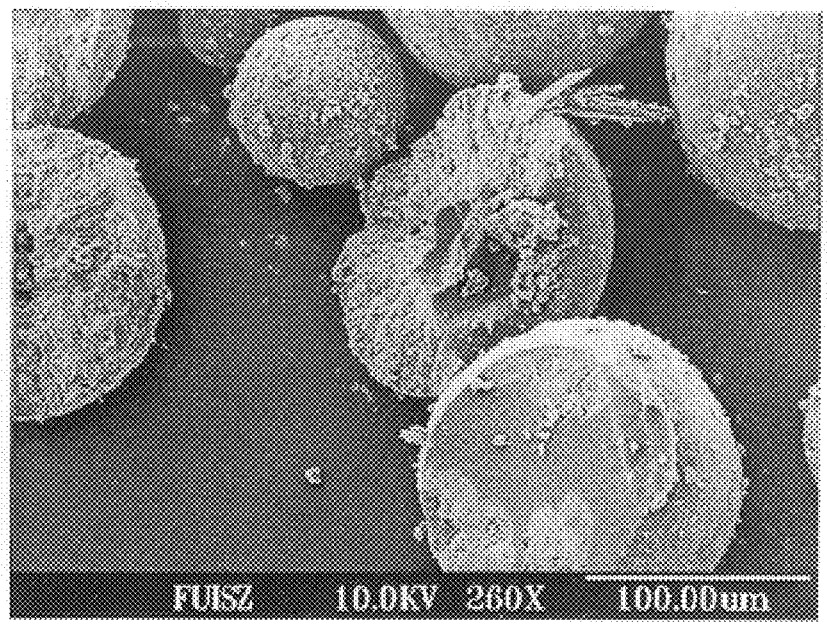
FIG. 3 is a 260x electromicrograph of 85:15 niacin:carnauba wax microspheres.
Figure 4:
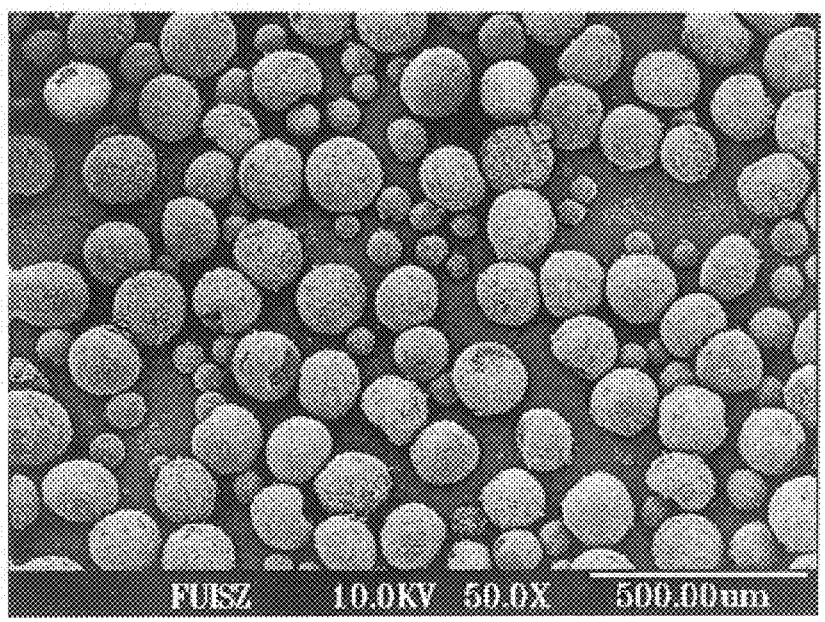
FIG. 4 is a 50x magnified micrograph of 85:15 niacin:carnauba wax microspheres.

FIGS. 1 and 2 show 100% niacin spheres. FIGS. 3 and 4 show 85:15 niacin:carnauba wax spheres. In FIGS. 1 and 2, fine particles of niacin are visible on the surface of the sphere. Very few fine particles are visible in FIGS. 3 and 4.

The ratio of active agent to processing aid in the feedstock will vary from about 95:5 to about 5:95, with ratios of 95:5 to 80:20 being highly effective. It was found that when microspheres of 100% niacin were made, the spheres had unwanted powdered fines, or aerosolized particulates, on their surfaces. After cooling, these fines may become trapped in the coating or form separate coated microparticles, resulting in a portion of the niacin spheres remaining uncoated. Nonetheless, microspheres containing only minor amounts of processing aid(s) may be used.

When subjected to "liquiflash" conditions, the blend of niacin and wax produced very few fines on the sphere surfaces. These spheres are readily coated to yield completely encapsulated spheres.

The active agent/wax combination yields monodispersed microspheres having minimal fines on their surfaces.

Also, due to the presence of the wax ingredients, the microspheres of active agent are more robust, i.e., less friable, than those made without wax. They stand up to coating and tableting with far less breakage than spheres made of 100% drug. Lastly, spheres have a more narrow particle size distribution when compared to those made without wax. This makes it easier to predict the quantity of drug in each coated unit.

The Coatings

To achieve taste-masking/sustained-release effects, the microspheres are coated with a blend of polymers, at least two of which have different levels of hydrophilicity. Generally, one polymer is more hydrophilic than the other. More hydrophilic polymer coatings generally produce dosage forms which dissolve faster. Conversely, less hydrophilic polymers give coatings which dissolve relatively slowly. Applicants believe that the combination of polymers with different hydrophilicities produces coatings which dissolve in a sustained fashion, i.e., over longer periods of time.

Typically, the more hydrophilic polymer is polyvinylpyrrolidone (PVP), hydroxypropylcellulose polymer, or a similar polymer. PVPK-30, manufactured by BASF, and Klucel EF, manufactured by Aqualon, are suitable. Mixtures are operable.

The less-hydrophilic polymer component is typically a cellulosic polymer. Useful cellulosic polymer ingredients include one or more polymers selected from ethyl cellulose (EC), polymethyl(meth)acrylate and the like and mixtures thereof. Ethocel (E-45) (Dow) works well.

The blend of polymers will typically be one in which the ratio of the less-hydrophilic polymer to the more-hydrophilic polymer is from about 90:10 to about 30:70. Taking ethyl cellulose (EC) polymer and polyvinylpyrrolidone (PVP) as examples, a suitable EC:PVP ratio will be about 60:40 to about 50:50, with 60:40 being highly effective.

For niacin-containing micropsheres, a blend of EC and PVP polymers is preferred.

For aspirin-containing microspheres, a blend of hydroxypropylcellulose and ethyl cellulose polymers is preferred.

The coating is applied to the microsphere substrates at a level of about 5% to about 45% by weight of the final dosage forms and coating levels of about 10% to about 25% by weight are typical.

Procedure

The invention involves procedures for:
(1) making the bio-affecting microspheres;
(2) coating the microspheres; and
(3) forming the coated particles into dosage forms.

Changes can be made in various aspects of the overall procedures described below.

Making the Microspheres

The microsphere substrate is made by subjecting a suitable feedstock to liquiflash spheronization conditions to produce solid monodispersed microspheres having particle sizes of about 500 microns or less. U.S. application Ser. Nos. 08/330,412, filed Oct. 28, 1994, and 08/755,811, filed Nov. 26, 1996, disclose the making of microspheres containing active agents. An apparatus suitable for making the spheres is disclosed in a U.S. application Ser. No. 08/874,215, filed Jun. 3, 1997, entitled A SPINNER HEAD HAVING FLOW RESTRICTING INSERTS. The disclosures of these applications are incorporated herein by reference. Niacin/wax spheres are typically made at temperatures of about 130° C. to about 240° C. and at a rotational speed of about 1800 rpm to about 4800 rpm.

Other procedures for making spherical particles can be employed.

Coating the Microspheres

Coating procedures conventionally used in the pharmaceutical industry can be employed. Useful coating techniques include Wurster coating and the like.

Suitable devices for coating the microspheres include fluidized bed coaters. Coating generally takes place at about 20° to about 30° C.

When solvents are employed, they are generally selected from water, acetone, isopropyl alcohol and the like. About 0% to about 20% of one or more plasticizers such as dibutyl sebacate, triethyl citrate or the like can be employed.

Anti-tacking agents, to prevent agglomeration of coated spheres, are also useful. Typical agents of this type are talc, colloidal silica, magnesium stearate and the like. When used, these agents are present in amounts of about 0% to about 50%.

While the use of multiple coatings is contemplated, the microspheres are typically coated once.

Production of Dosage Forms

The coated microspheres are usually used in a time-release dosage form. Suitable dosage forms include capsules, tablets, suspensions, and powders. Capsules and tablets are very effective.

The chemical composition of the capsule is not critical so long as its solubility is such that the coated spheres may be dissolved and absorbed by a host. Gelatin and/or cellulosics are usually used to make capsules suitable for containing the coated spheres of the invention. Other materials can be used.

EXAMPLES

The following examples illustrate the invention:

EXAMPLE I

Niacin Microspheres

One kilogram of an 85:15 blend of niacin and carnauba wax was mixed in a high-shear mixer. The mix was spheronized using liquiflash processing in the device described below at 50Hz speed at temperatures of 130° C. to 240° C.

The spheres were made using the device described in U.S. Ser. No. 08/874,215, filed Jun. 13, 1997. The disclosure of that application is incorporated herein by reference.

The spheres were yellow and had good surface morphology. Some surface particles were present. Surface electron microscopy showed no surface defects.

EXAMPLE II

Coated Microspheres

A coating formulation of ethyl cellulose:polyvinylpyrrolidone (60:40) was applied at 12.5% coating level in a fluidized bed coater (Glatt GPCG-1), to the spheres of Example I with a Wurster column. The ethyl cellulose and polyvinylpyrrolidone polymers were dissolved in acetone and sprayed on the microspheres at 23 degrees C. at a rate of 12–16 g/min.

EXAMPLE III

Dosage Forms

Microspheres equivalent to 500 mg niacin were encapsulated in size 000 gelatin capsules using a Perry Accufil manual filling machine.

EXAMPLE IV

Dissolution Studies

Three samples of 500 mg capsules containing EC/PVP coated microspheres (designated A, B and C below) were made in accordance with Example II and subjected to dissolution testing.

The dissolution testing was performed using USP apparatus II at 50 rpm with 900 mL distilled water for up to 22 hours.

The results are shown in the following table:

| TIME (HRS) | SAMPLE A | SAMPLE B | SAMPLE C |
|---|---|---|---|
| 1 | 23 | 35 | 13 |
| 3 | 60 | 70 | 39 |
| 6 | 79 | 85 | 56 |
| 9 | 89 | 93 | 69 |
| 12 | 95 | 97 | 80 |
| 22 | 101* | 101* | 99 |

*theoretical

EXAMPLE V

Coated Aspirin Microspheres

Using the procedure of Example I, microspheres containing aspirin and carnauba wax were prepared. They were then coated with a blend of hydroxypropylcellulose and ethylcellulose polymers.

EXAMPLE VI

Aspirin Dosage Forms

Microspheres made according to Example V are used in the production of sustained capsules and tablets.

Reasonable variations, such as those which would occur to a skilled artisan, can be made herein without departing from the scope of the invention.

We claim:

1. A composition suitable for making a sustained release dosage unit comprising suitable amounts of:
    (A) microspheres produced by imposing liquiflash conditions on a binary feedstock containing an active agent and processing aid; and
    (B) a coating containing a blend of polymers having different levels of hydrophilicity.

2. The composition of claim 1 wherein the active agent is niacin and the processing aid is carnauba wax.

3. The composition of claim 2 wherein (B) contains a blend of hydroxypropylcellulose and ethylcellulose polymers.

4. The composition of claim 3 wherein (A) is aspirin.

5. The composition of claim 2 wherein the less hydrophylic polymer is an ethylcellulose polymer or a poly(meth)acrylate polymer and the more hydrophilic polymer is polyvinylpyrrolidone or a hydroxypropylcellulose polymer.

6. The composition of claim 5 wherein (A) is niacin.

7. A method of making a dosage unit comprising the steps:
    (1) subjecting a binary mixture consisting essentially of an active agent and a processing aid selected from the group consisting of waxes to liquiflash conditions to yield microspheres, wherein the weight ratio of said active agent to said processing aid is in the range of 95:5 to 80:20;
    (2) coating the microspheres of step (1) with a blend of polymers having different levels of hydrophilicity.

8. The method of claim 7 wherein the active agent is selected from niacin, acetaminophen and aspirin.

9. The method of claim 8 wherein the active agent is niacin and the processing Aid is carnauba wax.

10. The method of claim 9 wherein the less hydrophylic polymer is an ethylcellulose polymer or a poly(meth)acrylate polymer and the more hydrophilic polymer is polyvinylpyrrolidone or a hydroxypropylcellulose polymer.

11. The method of claim 10 wherein the dosage unit made has sustained release properties.

12. The dosage unit made by the method of claim 8.

13. The composition of claim 1, wherein said blend comprises two polymers such that the ratio of the less hydrophilic polymer to the more hydrophilic polymer is within the range of about 90:10 to 70:30.

14. The composition of claim 13, wherein said less hydrophilic polymer is an ethylcellulose polymer and said more hydrophilic polymer is a polyvinylpyrrolidone.

* * * * *